US005099002A

United States Patent [19]

Rubinstein

[11] Patent Number: 5,099,002
[45] Date of Patent: * Mar. 24, 1992

[54] SEQUENTIAL IMPROVED METHOD FOR TREATMENT OF HUMAN BLOOD-CLOTTING FACTOR PRODUCTS

[75] Inventor: Alan I. Rubinstein, Los Angeles, Calif.

[73] Assignee: University of Southern California, Los Angeles, Calif.

[*] Notice: The portion of the term of this patent subsequent to Mar. 17, 2009 has been disclaimed.

[21] Appl. No.: 193,499

[22] Filed: May 12, 1988

Related U.S. Application Data

[63] Continuation-in-part of Ser. No. 50,153, May 15, 1987, abandoned.

[51] Int. Cl.⁵ .................. A61K 35/14; C07K 15/00
[52] U.S. Cl. ................... 530/381; 530/382; 530/383; 530/384; 530/380; 424/530; 514/8; 514/12; 514/21
[58] Field of Search ............ 424/101; 530/380, 382, 530/383, 381; 435/2; 514/8, 12, 21

[56] References Cited

U.S. PATENT DOCUMENTS 4,456,590  6/1984  Rubinstein ............... 424/101
4,556,558  12/1985  Rubinstein ............... 424/101

Primary Examiner—Margaret Moskowitz
Assistant Examiner—R. Keith Baker
Attorney, Agent, or Firm—Natan Epstein

[57] ABSTRACT

Factor VIII concentrate, or Factor IX concentrate, or fibrinogen concentrate, or other clotting-factor product, is subjected to a sequence of heating steps to reduce the infectivity of a virus (such as hepatitis- or AIDS-causing virus), if present. The heating is performed while the concentrate is lyophilized (or dried by another process). The heating steps in the sequence are for two or more different times, and at two or more different temperatures. After the heating sequence, the concentrate is reconstituted for use. This sequential method contemplates greater inactivation of different viral forms, or reduction of the heating required, or both. Reduction of heating requirements may appear as reduced overall heating time, or reduced aggregate power consumption, or both. Advantages include heightened quality-control assurance level. Also possibly, the invention offers some potential for preparation of vaccines against the virus, if sufficient quantity of the virus is present in the concentrate.

4 Claims, No Drawings

SEQUENTIAL IMPROVED METHOD FOR TREATMENT OF HUMAN BLOOD-CLOTTING FACTOR PRODUCTS

RELATED APPLICATION

This is a continuation-in-part of U.S. patent application Ser. No. 07/050,153, filed May 15, 1987, abandoned.

BACKGROUND

1. Field of the Invention

This invention relates generally to preparation of blood products for therapeutic use; and more particularly to methods for reducing the infectivity of a virus in human blood-clotting factor products. The method is of particular interest in regard to viruses that cause various forms of hepatitis or that cause acquired immune deficiency syndrome ("AIDS"); and also cytomegalovirus.

2. Prior Art

Isolation of clotting factors in human blood has been indispensable in understanding the pathology of hemophilia and other inherited bleeding disorders. Concomitantly, development of plasma-fractionation schemes for obtaining practical quantities of clotting-factor concentrates has provided important therapeutic tools for such disorders.

Transfusion therapy employing Factor VIII and Factor IX concentrates in particular has proven quite successful in ministering to hemophiliac patients. Under some circumstances, fibrinogen too has therapeutic value. Other clotting factors too are important.

Unfortunately, however, one serious drawback remains associated with transfusion therapy: risk of transmitting hepatitis viruses, AIDS viruses and cytomegalovirus. These viruses include (but are not limited to) hepatitis B virus, the virus known as "hepatitis non-A, non-B virus(es)," and hepatitis delta agent; and the viruses now believed to be causative agents of AIDS, denominated most commonly as HIV, but perhaps also including HIV-2, HIV-3 and HIV-4.

For definiteness of syntax I shall in this document refer to all such AIDS-causing virus or viruses as "AIDS virus." It will be understood, however, that this nomenclature encompasses perhaps more than one virus that may be involved.

Following is a brief description of the mechanisms by which viral transmission can occur in coagulation-factor transfusion therapy. I shall begin with the procedures used for preparing human coagulation-factor products. As is well known, such products usually take the form of human coagulation-factor concentrates, but my invention is not limited to concentrates.

Such concentrates are isolated from human blood plasma, by any of various processes called "plasma fractionation." A typical fractionation scheme is described in *Seminars in Thrombosis and Hemostatis*, volume VI number 1, page 4 (1979). This process yields cryoprecipitate and supernatant—the former fraction constituting a source of both Factor VIII concentrate and fibrinogen, and the latter fraction a source of Factor IX concentrate in addition to Factor II, VII and X concentrates.

As Gerety and Eyster have demonstrated by their contribution "Hepatitis Among Hemophiliacs," in Non-A, non-B Hepatitis, pages 103 through 106 (1981), hepatitis B virus initially present in whole plasma is distributed to the Factor VIII and Factor IX derivatives during the plasma-fractionation process. As also demonstrated by Maynard and Bradley's paper "Transmission by Blood Products," in the same book at pages 78 and 79, non-A, non-B hepatitis exists in both Factor VIII and IX derivatives.

Thus in simple terms, hepatitis viruses survive the processes used to prepare coagulation-factor concentrates. It is well known that AIDS virus too can be transmitted by Factor VIII and IX concentrates which have not undergone viral inactivation. Cytomegalovirus also may be of concern. Considering hepatitis, AIDS and possibly cytomegalovirus, there is a clear risk of viral infection by coagulation-factor transfusion.

This risk is a serious one. It is serious because a large number of plasma donors is required for commercial "pooled" production of clotting-factor concentrates. In absolute terms, if one donor is infected then possibly the entire supply may be infected, although for various reasons even this can be uncertain.

It is further uncertain to me whether "dilution" of one infected donation in the pool of donations diminishes the risk of infection from that one donation. Even if it does, the quantitative effect is speculative.

Typically the number of donors contributing to a pooled supply does not exceed a few hundred or a few thousand. Hence such dilution in the pool does not normally exceed two or three "logs" (factors of ten). Furthermore, if such a pool has infected donations, then the number of logs of effective dilution may be thereby reduced.

What is generally considered necessary is reduction of viral concentrations by several logs. Thus purity can only be guaranteed by assuring that all the donors are virus free, or by a disinfection procedure that is effective.

Viral transmission by heat-stable plasma components—that is, components other than those related to blood coagulation—can be controlled with comparative ease. Heating the stable components at moderate temperatures and for moderate times suffices to substantially inactivate some of the most troublesome viruses.

For example, hepatitis transmission by albumin can be prevented by heating the albumin in solution at sixty degrees Centigrade for ten hours. Preliminary propositions for similarly inactivating hepatitis viruses in immune globulin by such pasteurization have also been reported—though, to the best of my knowledge, nowhere in the world is a product available from such a procedure, and nowhere have details of how to produce such a product appeared (Welch, A. G. et al., "Non-A, Non-B Hepatitis from Intravenous Immunoglobulin," 1983 *Lancet* page 1198).

Unfortunately, however, similar efforts to treat clotting-factor concentrates in solution have failed. First, heating of the concentrates alone in solution is believed to markedly reduce or eliminate clotting-factor activity in the concentrates.

Factor VIII concentrate is known to have a very brief half-life even relative to some other coagulation-related factors. The fragility of Factor VIII and its related heat-instability have in the past presented serious impediments to developing virus-free Factor VIII concentrate, even while progress in removing hepatitis virus from other plasma fractions was being made.

Secondly, and more recently, highly purified Factor VIII precipitate has been dissolved in a solution of sucrose glycine and then, while in solution, heated for ten hours at sixty degrees. (All temperatures in this document are expressed in Centigrade degrees.) Although the Factor VIII concentrate subsequently derived from the heated precipitate does retain clotting factor activity, the yields obtained using this approach are very low—e. g., about eight percent (8%).

This work is reported by Heimburger et al. Their papers appear in *Hemostasis*, volume 10 supplement 1, page 204 (1981); and in the journal *Blut*, volume 44, pages 249 through 251 (1982).

Therefore, heating in solution does not appear to offer a practical answer to the problem of hepatitis and AIDS transmission by clotting-factor transfusions. The art and science of coagulation therapy, however, has already moved beyond such pasteurization techniques.

In particular a prior patent of the present inventor, U.S. Pat. No. 4,456,590, discloses a method for inactivating viruses present in Factor VIII and IX concentrates. In that process the concentrates are lyophilized (freeze dried), then heated while they remain in the lyophilized state, and eventually reconstituted for therapeutic use.

The lyophilized condition is believed to enhance stability of the concentrates during the heating step. Once lyophilized, the concentrates are heated for very extended periods of time, usually at moderate temperatures.

For example, one major United States manufacturer of clotting-factor concentrates heats the material, while it is lyophilized, at sixty degrees for thirty hours. Another manufacturer heats Factor IX at that temperature for approximately 144 hours. Still another manufacturer heats Factor VIII at sixty-eight degrees; in England, however, the preferred standard for Factor VIII treatment appears to be eighty degrees for seventy-two hours.

Not only the lyophilization-and-heating technique generally, but also these specific time-and-temperature combinations in particular, thus have attained acceptance by some workers in clotting-factor therapy. It must be appreciated that regulatory agencies in the United States and elsewhere continue to exercise very extensive control over the particular parameters used in all such disinfection techniques.

Any such procedure must perform the function of discriminating between viruses and clotting factors. It must inactivate the viruses to a satisfactory extent, while leaving the activity of the factors intact to a satisfactory extent. Furthermore the resulting clotting-factor product must be safe for human intravenous administration.

Hence a particular combination of parameters must be tested in extensive and costly clinical trials to establish that it satisfies all three of these criteria reliably. Once so tested, a specific procedure cannot be varied without risk of undermining one or another of the three established assurances.

Regulatory agencies may accordingly refuse to allow a manufacturer who heats at sixty degrees for thirty hours to raise the temperature to sixty-four degrees. This is so even though another manufacturer already employs sixty-eight degrees.

Such an intermediate temperature might seem very probably safe and effective; nonetheless, it has not been fully tested. Accordingly the continuation of strict regulatory control is justified.

This continuing control establishes a very definite and restricted set of times and temperatures that are accepted by regulatory agencies as:

(1) adequate for at least some disinfection of lyophilized concentrate, (2) essentially nondamaging to lyophilized concentrate, and (3) safe to the product recipient.

In the remainder of this document—and particularly in the claims which follow this disclosure—all references to "accepted" times or temperatures mean those definite parameter values that have been accepted by regulatory agencies for clinical use.

In adopting this definition of "accepted" time or temperature I do not mean to limit myself to the four time-and-temperature examples that have been stated above. From time to time, manufacturer to manufacturer, and country to country, many other specific values of time or temperature have been or will be so "accepted."

Heat treatment of lyophilized Factor VIII and IX concentrates is in my opinion the most economical and best procedure heretofore available for disinfection against hepatitis and AIDS. In addition it does not introduce any potentially toxic chemicals to inactivate the viruses in the concentrate.

Nevertheless, this procedure like any is subject to improvement. Further quality assurance, if obtained cost-effectively, is always desirable. Moreover, some workers have suggested that inactivation of hepatitis viruses by the method of my prior patent may need some improvement in increasing viral inactivation at some time-and-temperature combinations—particularly those involving relatively short times and low temperatures.

Another area for improvement is that of certain very slight variations in treatment conditions. Laboratory procedures in blood-banking practice are generally excellent, and scrupulously followed. Certain obscure opportunities for marginal performance, however, can creep into even the best procedures.

Some of these variations may be essentially uncontrolled—or even uncontrollable. For example, an incubator, water bath or oven is sometimes used for heat-treating a large number of discrete quantities of clotting-factor concentrate together, at the same time. Despite good design, temperature within a heating system is never perfectly uniform. As the equipment ages, subtle changes can perhaps compound the nonuniformity of temperature.

As a result, those discrete quantities (in individual jars, watchglasses, or otherwise) of clotting-factor concentrate placed in certain parts of the heating system may not reach the same temperature as others. In short, heating conditions are subject to slight variation from quantity to quantity.

If the variation is between, say, one and three degrees, treatment of those particular quantities of clotting factor might be considered marginal. Therefore, to provide a natural opportunity for minimizing the effects of such uncontrolled variations would be desirable.

Certain information that appears in the literature will be introduced here. I refer to a paper by Piszkiewicz et al., "Heat Inactivation of Human Immunodeficiency Virus in Lyophilized Anti-Inhibitor Coagulant Complex ("Autoplex ®")," in *Thrombosis Research* volume 44, pages 701 through 707 (1986).

The Piszkiewicz article, and earlier papers to which it refers, show that viral inactivation does not follow a simple exponential function. In other words, inactivation does not continue at a constant rate, or fractional reduction, relative to the infectivity at each time.

Rather, as the treatment proceeds the inactivation decelerates (even as compared with exponential decay). Most of the viral inactivation occurs in initial periods of heating, and particularly in the first hours. Piszkiewicz fails to suggest any way to use these observations or conclusions to improve disinfection techniques.

SUMMARY OF THE DISCLOSURE

My invention is a method of treating human blood-clotting factor concentrate to reduce the infectivity of a virus, such as hepatitis- or AIDS-causing virus or cytomegalovirus, if present. The method includes these steps:

(1) lyophilizing the concentrate or obtaining the concentrate prelyophilized;
(2) then heating the concentrate, while it is lyophilized or prelyophilized, for and at a plurality of different time-and-temperature combinations; and
(3) then reconstituting the concentrate.

In step (2) above, I use the phrase "heating ... for and at ... different time-and-temperature combinations". In this phrase the word "for" is associated with the word "time"; and the word "at" goes with "temperature." Thus I intend the phrase to mean, in a shorthand way, treatment by two or more different heatings, each for a particular time and at a particular temperature in combination.

The foregoing may be a definition of my invention in its broadest or most general form. For greatest enjoyment of its potential benefits and advantages, however, I prefer practice of the invention with a number of additional features or characteristics.

For example, I prefer that the different time-and-temperature combinations occur in a sequence of progressively higher temperatures. I also prefer to provide the different time-and-temperature combinations in a sequence of progressively shorter times. Both these conditions can be satisfied in a single sequence.

These characteristics are not necessary, however, and in some circumstances the opposite may be preferred—i.e., different time-and-temperature combinations occurring in a sequence of progressively longer times. That too is within the broad scope of my invention.

The temperatures and times used in my procedure can be advantageously selected so that the aggregate of all times in the plurality of time-and-temperature combinations is no larger than the time accepted as adequate for disinfection of lyophilized concentrate in a single-heating-step procedure. In other words, the quality-assurance benefits of the invention can be obtained without using more time or more energy.

In fact, I believe that that aggregate time can be made notably smaller than the time accepted as adequate for disinfection of lyophilized concentrate in a procedure using a single heating step. Further, I believe that this can be done without sacrificing clotting-factor activity or patient safety.

Similarly at least one temperature is advantageously chosen no lower than a temperature accepted as nondamaging to lyophilized concentrate (and noninjurious to patients) in a single-heating-step procedure of adequate duration. A benefit of my present invention, however, is the ability to make judicious and controlled use of at least one temperature that is considerably higher than, or at least near, the accepted temperatures.

My invention also offers an incidental benefit which can be used if desired. The end of each heating subcycle at a particular time-and-temperature combination can be used as a convenient stage for removal of the multiple quantities of clotting-factor product from the oven and in essence shuffling them for replacement in the oven.

This removal, rearrangement and replacement is an additional step, performed between at least two of the time-and-temperature combinations. Stated in more abstract terms, the step consists of decorrelating the discrete quantities of product, at least to some extent, with respect to any slight variation of conditions that may be occurring.

Hence if, for example again, the oven temperature is nonuniform, no one sample is likely to be treated at a low temperature for the entire multiple-heating procedure. This general principle applies to and may moderate the effects of other kinds of variations—even some that may not be recognized at all.

The foregoing illustrates the important fact that the various time-and-temperature combinations need not all take place in continuous sequence. Any two time-and-temperature combinations may be separated, as convenient, by another distinctly different procedural step.

Such a step could be, for example, storing at room temperature, or refrigerating, or packaging, or reconstituting and redyhdrating, or shipping. I also mean to encompass any combination of such distinctly different procedural steps.

In a variant or alternative embodiment of my invention, other drying methods perhaps can be substituted for lyophilization. For example, spray drying and vacuum drying can possibly be used; however, care must be exercised to ensure that the amount of moisture removed from the plasma derivatives by these methods is sufficient to render them heat-stable. Also, care should be taken that the clotting factor concentrate itself is not altered or damaged.

Additional care may be required when spray drying or vacuum drying of Factor VIII concentrate is contemplated. Factor VIII is a large and relatively complex molecule, and may be unacceptably damaged by these techniques unless special precautions are taken. For this reason, lyophilization is the preferred mode of removing moisture from Factor VIII concentrate preparatory to heating.

My present invention arises from the general recognition that improvement of the procedure introduced in my above-mentioned patent may be in order. More specifically, I believe that the procedure introduced in my earlier-mentioned patent perhaps can be refined in two regards: efficacy of viral disinfection, particularly for some viral strains or forms; and cost-effectiveness.

I believe that selective and "targeted" use of treatment time has not heretofore been adequately considered. I submit that the several forms of AIDS virus and several forms of hepatitis-causing virus, and cytomegalovirus if present, can be inactivated most effectively—and also most cost-effectively—by directing different segments of the treatment more specifically to different viral forms.

In particular, data such as that of Piszkiewicz shows that much greater inactivation rates are obtained in the beginning of the treatment. Quite simply, if one can always operate at the high rates associated with this "beginning" condition, then:

a much higher assurance of viral inactivation can be obtained for a given expenditure of time and power; or much less time and power can be expended for the same assurance of viral inactivation; or a suitable tradeoff can be found that produces significantly higher assurance for significantly less time and power.

As another basis for my belief that efficacy and cost-effectiveness of disinfection should both be improved, I submit that the several forms of hepatitis or AIDS virus must surely have respective different sensitivities to heat —and, more specifically, to temperature.

In fact, it would seem that data such as that in Piszkiewicz's FIG. 1 are possibly interpretable as the superposition of simple straight-line graphs for three or more phenomena. (A straight line on Piszkiewicz's semilog presentation corresponds to a simple exponential decay.) The various straight lines would have different negative slopes.

The different slopes would in turn correspond to respective numerical-decay time constants, that differ by orders of magnitude. Such a model would seem not only to fit the Piszkiewicz data but, if correct, also offer an approach to calculating the likely effects of various candidate treatment schedules.

My method described herein, however, does not depend on the physical accuracy of this interpretation. I am merely noting simple observations regarding Piszkiewicz's data. Other possible models are discussed in detail below and shown to be compatible with my present invention.

The heretofore-employed procedures address only a single combination of time and temperature to a great multiplicity of different viral agents. Those procedures thus are extremely nonspecific in their attack.

Infectivity reduction of those procedures therefore is possibly:

(1) for some viruses, "overkill" (that is, reduction of their infectivity far beyond levels at which they pose real threats), while (2) for some other viruses, at best marginal.

This latter assertion is particularly likely to be true for those viruses whose initial and final quantities are both relatively near to detection limits, and especially those which unbeknownst to current medical science are not detected by conventional present assays.

DETAILED DESCRIPTION OF TESTS AND OF THE PREFERRED EMBODIMENTS

I have performed preliminary tests to determine whether significant recovery of clotting factor could still be obtained after plural heating cycles. The tests were conducted, in particular, at escalating temperatures.

Test Conditions and Procedures

I obtained paired samples of lyophilized Factor VIII and IX concentrates, which had previously been heat-treated at approximately sixty to sixty-eight degrees in the lyophilized state by the manufacturer. Within each pair, the two samples had identical lot numbers and were considered to be substantially duplicates.

The samples generally weighed less than one hundred grams each, and were packaged in vials of volume ranging from fifty to ninety milliliters.

One sample in each pair was heated, by placing the sample vial in a dry oven at a first predetermined temperature at ambient room pressure for a first predetermined period of time. This temperature was seventy or seventy-three degrees for Factor VIII, and eighty degrees for Factor IX.

The remaining sample in each pair served as a control. It was refrigerated at four to six degrees during the heating of its duplicate.

After the heat treatment, some of the samples were again heated, but at a second predetermined temperature. This temperature was eighty or eighty-two degrees for Factor VIII, and eighty or ninety-two degrees for Factor IX. Both the control and heat-treated samples were then reconstituted with sterile water.

(In these tests, reconstitution was generally carried out according to manufacturer's specifications. The solubility of some heat-treated clotting factors, however, may possibly be improved by increasing the amount of sterile water used during reconstitution, over that recommended by the manufacturer.)

As shown in Table 1, two Factor VIII samples were each heated once at a common temperature but for different times and then assayed for activity. Two other samples were each heated twice—each for two different time periods and at two different temperatures—and then similarly assayed.

TABLE 1

Factor VIII activity, after multiple heating of concentrate while lyophilized

| Lot | Temperature (degrees C.) | Time (hrs.) | Dilution (1:) | Activity |
|---|---|---|---|---|
| A 8-0420 | control | | 100 | 1350 |
| | | | 200 | 1340 |
| | | | 400 | 1740 |
| | 70 | 10.5 | 100 | 1000 |
| | | | 200 | 1040 |
| | | | 400 | 1200 |
| | 70 | 12 | 100 | 1000 |
| | | | 200 | 1210 |
| | | | 400 | 1480 |
| | 70 and then 80 | 12 2 | — 100 | — 1000 |
| | | | 200 | 1340 |
| | | | 400 | 1109 |
| 505083 | control | | 200 | 1109 |
| | | | 400 | 1566 |
| | | | 800 | 1556 |
| | | | 1600 | 1873 |
| | | | 3200 | 1696 |
| | 73 and then 82 | 10.27 1 | — 200 | — 1127 |
| | | | 400 | 1394 |
| | | | 800 | 1397 |
| | | | 1600 | 1203 |
| | | | 3200 | 1310 |

TABLE 2

Von Willebrand Antigen recovery, after multiple heating of Factor VIII concentrate while lyophilized

| Lot | Temperature (degrees C.) | Time (hrs.) | Dilution (1:) | Result (%) |
|---|---|---|---|---|
| 505083 | control | | 2000 | 6476 |
| | | | 4000 | 7220 |
| | | | 8000 | 7808 |
| | 73 and then 82 | 10.27 1 | — 2000 | — 7056 |
| | | | 4000 | 6812 |
| | | | 8000 | 6928 |

These assays were carried out using the one-stage Factor VIII assay. The Factor VIII assay performed on lot 505083 was a one-stage clot-detection assay on General Diagnostics X-2.

As shown in Table 2, one of the above-mentioned Factor VIII samples, after the treatment, and its duplicate were also assayed for Von Willebrand Antigen recovery. This antigen is related to Factor VIII.

The Von Willebrand Antigen assay was an in-house adaptation by Scripps Clinic and Research Foundation (La Jolla, Calif.) of the Elisa Method of using the Stago Von Willebrand Antigen kits (marketed by American BioProducts).

As shown in Table 3, similar treatments and assays were performed on two Factor IX samples. The Factor IX was a one-stage standard assay.

The lot appearing in Table 1 coded with prefix "A" was manufactured by Alpha Therapeutics and are believed to have been heated at approximately sixty degrees. All the other lots were obtained from Cutter Laboratories and are believed to have been heated at approximately sixty-eight degrees.

TABLE 3

Factor IX activity, after multiple heating of concentrate while lyophilized.

| Lot | Approx. Temp. (degrees C.) | Time (hrs.) | Activity (%) |
|---|---|---|---|
| 205003 | control | | 1573 |
| | 80 | 11 | 1347 |
| | 80 | 11 | — |
| | and then | | |
| | 92 | 1.15 | 1280 |

Test Results and Conclusions

The results summarized in Table 1 show that a commercial lyophilized Factor VIII concentrate that had been heated in the lyophilized state by the manufacturer, and then heated again at temperatures greater than sixty degrees while lyophilized, still yielded significant recovery of Factor VIII. Additionally these results demonstrate that the concentrate may be heated more than twice at different temperatures for various times and still yield significant Factor VIII recovery.

(It may be noted that in table 1 for dilutions 1:200 and 1:400 there appear increases in the activities reported for twelve hours as compared with 10.5 hours. Similarly there appear increases at seventy-degrees-and-twelve-hours plus eighty-and-two, as compared with seventy-and-twelve alone. No real increase in activity can be explained as a result of the heat treatment. The statistical error in the assay, however, is on the order of the anomalies observed; and moreover the single-stage assay itself may produce some spurious activation.)

Table 2 shows similarly that Von Willebrand Antigen associated with the Factor VIII concentrate is not significantly reduced after the multiple heating. Table 3 establishes for Factor IX activity a like conclusion—namely, that following multiple heat treatment in the lyophilized state there was significant recovery.

I conclude that plasma fractions such as Factor VIII and IX concentrates of varying purity can be repeatedly heat-treated in lyophilized form, at different elevated temperatures and for extended periods of time, without significantly impairing clotting activity.

Through suitable adjustment of times and temperatures within the ranges reported, or alternately by suitable extrapolation beyond those ranges, time-and-temperature combinations can be established for effective and safe heat-sterilization of plasma fractions.

Furthermore, visual observations confirm that the solubility of lyophilized Factor VIII and IX concentrates is not deleteriously affected by the high-temperature heat-treatment of the present invention. The amount of diluent added in reconstitution can be increased until complete solubility is achieved.

The latter observation is important from a practical standpoint. Typically, bulk manufacturers of lyophilized clotting-factor concentrates and other plasma derivatives instruct end-users to carry out resolubilization of the lyophilized concentrtes with specified amounts of diluent —e. g., sterile water, saline solutions or the like. The specified amounts have been empirically determined to ensure adequate solubility of the concentrates upon reconstitution.

If, however, an attempt to resolubilize a heat-treated lyophilized concentrate according to manufacturer's specifications yields a solution of unacceptable viscosity, more diluent can be added. Addition of an appropriate diluent in excess of the amount previously thought necessary for solubility—that is, in excess of that recommended by the manufacturer—will in many cases result in complete solubilization of the concentrate. It will do so without destroying clotting-factor activity.

This ability to compensate for increased viscosity of concentrates heat-treated for extended periods at high temperatures greatly enhances the utility and commercial attractiveness of my invention. Given the knowledge that lyophilized concentrates which might otherwise be rendered unusable by heat treatment can nevertheless be recovered, temperatures and times for the treatment can be adjusted upward to the level required for more fully inactivating hepatitis virus of both the B type and the non-A, non-B type.

It will also be apparent from extrapolation of the test results presented above that the method of this invention can be performed at essentially any point during the plasma fractionation process. That is, at any point along the fractionation where a plasma or plasma derivative can be lyophilized, heat treatment can be performed—and the plasma or derivative resolubilized or reconstituted before continuing the fractionation.

Consider for example the case in which Factor VIII concentrate is ultimately derived from a plasma fractionation scheme such as that disclosed in Mammen, et al., "Treatment of Bleeding Disorders with Blood Components," Reviews of Hematology, volume I, page 144 (1980). In this situation, lyophilization and heat-treating is not limited to the Factor VIII concentrate.

It can also be performed on the whole plasma, on cryoprecipitate obtained from fresh frozen plasma, on clarified extract obtained from cryoprecipitate, and on the supernatant obtained from clarified extract. Selection of an appropriate point—or two or more distinctly different points—in the plasma fractionation for applying the heat treatment can then be based upon pragmatic considerations such as cost or convenience.

My invention thus represents a significant achievement in the field of blood technology. This is particularly true of Factor VIII, in view of its inherent instability previously mentioned.

Use of the present invention accordingly furnishes a practical, economic means for reducing the risk of viral transmission by clotting-fact or transfusion therapy.

DETAILS OF PREFERRED EMBODIMENTS

First I shall discuss various models that fit the reported inactivation phenomena. I shall show that any of three different theories is compatible with improved inactivation using my present invention.

Thereafter I shall discuss selection of temperature-and-time combinations for use in practicing my invention. This section will conclude with discussion of vaccines.

Most of the inactivation achieved by heating at any given temperature occurs near the beginning of heating. As suggested above, this may be due to removal of viral forms that are most sensitive to heat at that given temperature, leaving only those which are inactivated more slowly.

By using a higher temperature to attack the latter viruses, the same phenomenon—namely, rapid initial inactivation, followed by slower inactivation—can perhaps then be made to appear again. In actuality, however, it is possible that what happens is qualitatively different: the more heat-sensitive viruses may have already been taken out of the picture, and it is possible that in a sense all or most of the heat is being applied to the less heat-sensitive viruses.

Perhaps a more sophisticated view is that at this higher temperature more heat-sensitive viruses are being reduced in concentration by yet further very large factors, possibly even several logs. Nonetheless the pivotal idea remains that inactivation proceeds more rapidly at higher temperatures, and that higher-temperature treatment rapidly inactivates the less heat-sensitive viruses.

Other theories or models may be used in attempting to describe the inactivation phenomena reported—as well as the phenomena believed to occur in accordance with the present invention. For example, it may be that initial heating even at low temperatures has the effect of "priming" some viruses that are not completely inactivated at the lower temperatures, so that they are more susceptible to destruction at higher temperatures.

This general process of priming might take the form of, say, a sort of embrittlement. Here a short exposure to the higher temperature simply completes inactivation of the "embrittled" viruses, possibly much more rapidly than with continued exposure to the lower temperature.

Another possibility is that some viruses are in a sense embedded and sheathed within structures formed by others. In this model, denaturing those other structures breaks down the protective sheathing. Breakdown of the sheathing makes the embedded viruses more accessible to bombardment by fast-moving molecules of water or other small species (e.g., fragments of previously denatured proteins) in the matrix.

In either the embrittlement or the sheathing-breakdown model, however, there is room to explain the deceleration reported by Pizskiewicz and others. Specifically, debris from either embrittled viruses or denatured "sheathing" viruses may simply pile up and so become progressively more of a barrier to later viral inactivation.

Added agitation at the molecular level, introduced by higher temperatures, may disassemble this accumulated debris and reexpose the remaining viruses to heat-developed bombardment. Thus the resultant observable behavior might be similar to that of a multiple-species model.

In either case, applying one or more high-temperature treatments, for a short time—in addition to applying a lower-temperature treatment for a relatively long time—may be expected to invoke the steep initial part of the inactivation functions at both temperatures. This will both hasten the entire process of inactivation and provide superior overall reduction of infectivity.

Still another possibility is that two or more of these models are correct, operating in combination with one another and possibly in combination with still others. In this case the observed and expected behavior could occur as the result of two or more such groups of effects together. Once again, this discussion is of theories or hypotheses, and their truth has not been proven.

Chemists and biologists use various rules of thumb to compare the relative rapidity of chemical or life processes at different temperatures. Perhaps such approaches may be used to estimate the relative decrease in the viral-inactivation time-constant obtained through raising the temperature by, say, ten degrees. In any event, the time required to pass through the rapid-inactivation region at the higher temperature is readily found empirically.

Now the assay at the beginning of this second heating interval corresponds presumably to the concentration of the remaining viruses—whether less heat-sensitive viral forms, or embrittled viruses, or unsheathed viruses, or otherwise. This concentration is generally one or two logs lower than the initial assay at the beginning of the first heating interval.

Consequently, the number of logs' reduction required in this second heating interval—to reach a given target level of infectivity—may be smaller. This line of reasoning is somewhat analogous to that employed by Pizskiewicz at the end of his previously-discussed paper, in discussing the cumulative inactivation obtained by several different processes applied in series.

When the rate of inactivation again begins to level off in this second heating, once again it may be concluded that less-sensitive viral forms may have been largely eliminated, possibly leaving, let us say, extremely heat-resistant (or at least still-more heat-resistant) forms. Alternatively, again, debris accumulation and/or embrittlement may have proceeded to a point at which access for bombardment is obstructed.

Once again, irrespective of the model preferred, the remaining viruses are at a lower level of concentration than before both of the first two heatings. The present concentration may be perhaps another order of magnitude lower.

Hence the clock can be reset again, so to speak, for inactivation of this third viral form or group of forms—or, under any model, this third target population of viruses—by raising the temperature to a still higher value. Yet again, however, the length of time required for effective reduction of this third group is possibly shorter because of its initially lower concentration. Therefore the clock once reset need not run as long.

Some of the models as tentatively described above may seem to suggest that the plural or multiple time-and-temperature combinations employed should follow an escalating progression of temperatures. In such a scheme it would probably be most natural to expect a corresponding deescalating progression of heating times.

For the most part, however, at least some of these theories may be recouched in such a way as to suggest preferability of an escalating progression of times. Correspondingly, for such variant theories, a deescalating progression of temperatures would probably be preferred.

Yet other ways of modelling the phenomena may seem to suggest that both effectiveness and cost-effectiveness should be independent of the order in which the various time-and-temperature combinations are used. For all these reasons, my invention as broadly conceived is not to be limited to any particular sequence.

My own intuitive preference, however, is for those models which favor increasing temperatures and decreasing times. Furthermore the successful tests described above followed that pattern.

Finally, that pattern has the added pragmatic advantage that the first step of my new procedure can be made to correspond exactly or very closely, as preferred, to procedures that are already "accepted"—in the sense of that word defined earlier. Hence as a practical matter the additional testing required to obtain regulatory approval can possibly be confined to —or at least emphasize—the higher-temperature, shorter-interval treatments considered as "add-on" processes.

For these several reasons, in the appended claims I have emphasized rising-temperature, falling-time sequences. For the last reason in particular I have also emphasized sequences that are based upon the accepted procedures—thereby to avoid undue delays in the short-term commercialization of the present invention.

This reasoning is accordingly based upon economic considerations. Only a process that is economic is relatively likely to contribute to the progress of the useful arts. I consider these sequences critical to commercial use of my invention relatively soon.

On the other hand, for the longer term, limiting this invention to sequences that include one of the accepted procedures in toto would be to limit the benefits of the invention strictly to its added quality-assurance objectives. Those are of course very important, but I believe strongly that the potential of this invention for improved cost-effectiveness too should be developed fully.

That belief militates in favor of those time-and-temperature combinations which in the aggregate consume less time—and much less heating power as well. These combinations necessarily include sequences in which the longest single time is only a fraction, preferably a fraction significantly smaller than unity, of the times now accepted for single-heating-step treatment.

Accordingly in some of the appended claims I have also emphasized short-aggregate-time sequences, as well as high-temperature/short-time individual heatings. I consider these combinations particularly critical for use somewhat more remotely in the future.

Hence for example, for the near term, at least one treatment temperature that is very-generally over sixty degrees and at least one other that is significantly higher than sixty-five, would satisfy the relatively conservative requirement for basing the procedure on similarly-accepted treatments. The same is true for providing one treatment time significantly longer than twenty hours, and another treatment time significantly shorter than seventy-two hours.

Likewise directed to the near-term use of the invention is one combination of sixty to seventy degrees for twenty to seventy-two hours, together with another combination of over seventy degrees for fewer than thirty hours Perhaps finally heating at a very high temperature —e g., greater than eighty-five degrees—for less than one hour can be applied as one of the treatments.

Focused more on longer-term economics is one time significantly longer than ten hours, in combination with another significantly shorter than thirty. Both these values are rather short in comparison with accepted current practice.

It will be seen that these various ranges and range combinations are not mutually exclusive; in some cases, rather, they are nested or overlappnng. Furthermore, still other times and temperatures may be present in an actual treatment regimen, though not specifically recited, and those other times may be outside the ranges stated. In essence, therefore, the differences between the different critical combinations described above are primarily a matter of emphasis.

Still another way of stating a preferred embodiment of my invention is to recite a regimen of at least three (or more) time-and-temperature-range combinations. The three stated range combinations may encompass both the likely short-term commercial possibilities and the possible or probable longer-term options.

For example such a statement may call for:
- at least one time-and-temperature combination in the range of sixty to seventy degrees and ten to seventy-two hours;
- one other time-and-temperature combination generally in the range of seventy to eighty degrees and three to thirty hours; and
- at least one other time-and-temperature combination generally in the range of over eighty degrees and fewer than ten hours.

This set of specifications, using lower temperatures and longer times of each combination, will be seen to correspond to a treatment regimen based more closely on currently accepted single-heating treatment, with moderate "add on" processing. (I refer to sixty degrees for perhaps thirty to seventy-two hours, seventy for ten to thirty, and eighty for six to ten.) Its low-temperature and long-time range limits thus express a critically useful combination for commercialization relatively soon.

The same set, but using higher temperatures and shorter times also enumerated, corresponds to a more cost-effective and sophisticated application of the principles of my invention. (This might be, for example, seventy for ten to fifteen hours, eighty for three to eight, and ninety for, say, one or two.) Here the total treatment time is only fourteen to twenty-five hours, and the high-temperature/short-time range limits thus express a critically useful combination for commercialization somewhat later.

I wish to mention still another preferred embodiment, relatively conservative in treatment times but using somewhat elevated temperatures. That sequence is very generally sixty-eight degrees for thirty hours, seventy-five for fifteen, and eighty-five degrees for three hours.

This embodiment is one that might be considered for approval relatively soon, and that I believe would effectuate a very great improvement in quality assurance. Its aggregate time of fifty-three hours is not as strikingly short as some just mentioned; yet it is far less than the 144 hours accepted for one manufacturer's treatment of Factor IX, and considerably less than the seventy-two hours accepted in England for Factor VIII. Consequently for some applications or environments this embodiment though seemingly conservative offers marked improvement in cost effectiveness as well as in quality assurance.

I am a trained and experienced professional and I have expertise in the field of preparing blood products for therapeutic use, and in the particular area of reducing the infectivity of viruses in human blood-clotting factor products. I was formerly director of the hemostasis laboratory and associate director of the blood bank, and a member of the faculty, at University of Texas Medical School, Houston.

In my professional opinion, the method of my present invention will significantly reduce the infectivity of a virus, such as hepatitis- or AIDS-causing virus or cytomegalovirus, if present.

It is also my professional opinion that the method of this invention will increase the inactivation beyond the level obtained by any currently accepted heat-treating procedure involving a single time-and-temperature combination heat treatment of a clotting-factor product while lyophilized. The method of my present invention will do so, in my further professional opinion, without significantly reducing patient safety or the therapeutic value of the products.

Finally, there is some potential for using my invention to manufacture vaccine against, e.g., certain hepatitis- and AIDS-causing agents. As suggested earlier, hepatitis B virus and probably non-A, non-B hepatitis are distributed in the clotting-factor derivtives—particularly Factor VIII and IX concentrates.

Heat treatment of clotting-factor fractions in lyophilized or dried form at suitable temperatures for suitable periods of time can render any hepatitis virus that is present in the concentrates noinfectious. Such treatment, however, can perhaps be optimized so as to leave that virus still immuogenic.

Consequently, reconstituted heat-treated lyophilized coagulation-factor concentrates perhaps can function as hepatitis vaccines—while simultaneously providing the therapeutic benefits normally associated with clotting-factor fractions. Immunogenicity of such materials may be relatively weak, and accordingly their use as vaccines may require multiple doses over protracted calendar-scale periods of time.

It will be understood that the foregoing disclosure is intended to be merely exemplary, and not to limit the scope of the invention—which is to be determined by reference to the appended claims.

I claim:

1. A method of treating human blood-clotting factor product to reduce the infectivity of hepatitis- or AIDS-causing virus, said method comprising the steps of:
   lyophilizing the product;
   then heating the product, while it is lyophilized, at
   a first temperature below 80 degrees C. for up to 72 hours; and
   a second temperature which is above 80 degrees and up to 92 degrees for up to 1.15 hours; and then reconstituting the product.

2. The method of claim 1 further comprising one or more additional steps of heating the product, while it is lyophilized, at a temperature which is:
   below 80 degrees C. for a total heating time of the product of up to 72 hours at temperatures below 80 degrees C.; or
   above 80 degrees and up to 92 degrees for a total heating time of the product of up to 1.15 hours at temperatures between 80 degrees and up to 92 degrees.

3. The method of claim 1 further comprising the step of cooling the product to an ambient temperature between said heating steps.

4. The method of claim 2 further comprising the step of cooling the product to a generally ambient temperature between one or more of said heating steps.

* * * * *